United States Patent [19]

Netteland

[11] 4,253,455

[45] Mar. 3, 1981

[54] BREATHING VALVE ASSEMBLY WITH DIAPHRAGM CONTROL OF THE EXHAUST PORTS

[75] Inventor: Loyal G. Netteland, Holland, N.Y.

[73] Assignee: A-T-O Inc., Willoughby, Ohio

[21] Appl. No.: 931,537

[22] Filed: Aug. 7, 1978

[51] Int. Cl.[3] .............................................. A61M 16/00

[52] U.S. Cl. ................................................ 128/204.26

[58] Field of Search ............ 137/494, 505.38, DIG. 9, 137/102, 107; 128/142.2, 142 R, 142.3, 142.4, 141 R, 204.26

[56] References Cited

U.S. PATENT DOCUMENTS

| | | | |
|---|---|---|---|
| 2,387,123 | 10/1965 | Deming | 128/142 |
| 2,755,799 | 7/1956 | Marty | 128/142 |
| 2,843,120 | 7/1958 | Thaver | 128/144 |
| 3,242,921 | 3/1966 | Seeler | 137/DIG. 9 |
| 3,459,216 | 8/1969 | Bloom et al. | 137/512.1 |
| 3,467,093 | 9/1969 | Hotz et al. | 128/146.5 |
| 3,978,854 | 9/1976 | Mills | 128/142.2 |
| 4,147,176 | 4/1979 | Christianson | 128/142.2 X |

FOREIGN PATENT DOCUMENTS

| | | |
|---|---|---|
| 1214907 | 12/1970 | United Kingdom . |
| 1487676 | 10/1977 | United Kingdom . |
| 1487677 | 10/1977 | United Kingdom . |

*Primary Examiner*—Harry N. Haroian

*Attorney, Agent, or Firm*—Christel, Bean & Linihan

[57] ABSTRACT

A breathing apparatus having an exhaust valve and a diaphragm actuated inlet valve, wherein the exhaust valve includes a sealing surface against which the diaphragm normally is sealingly engaged to close the opening and from which the diaphragm is disengaged upon exhalation to open the exhaust valve.

13 Claims, 4 Drawing Figures

Fig. 3.
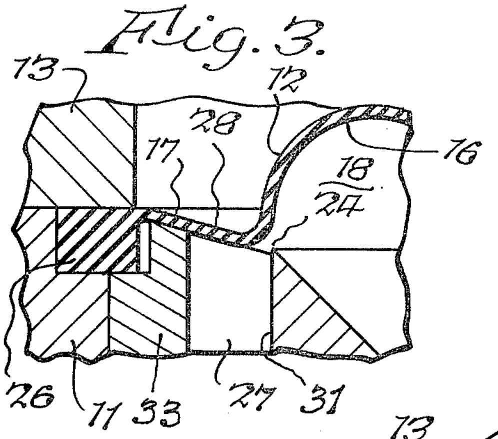
Fig. 1.
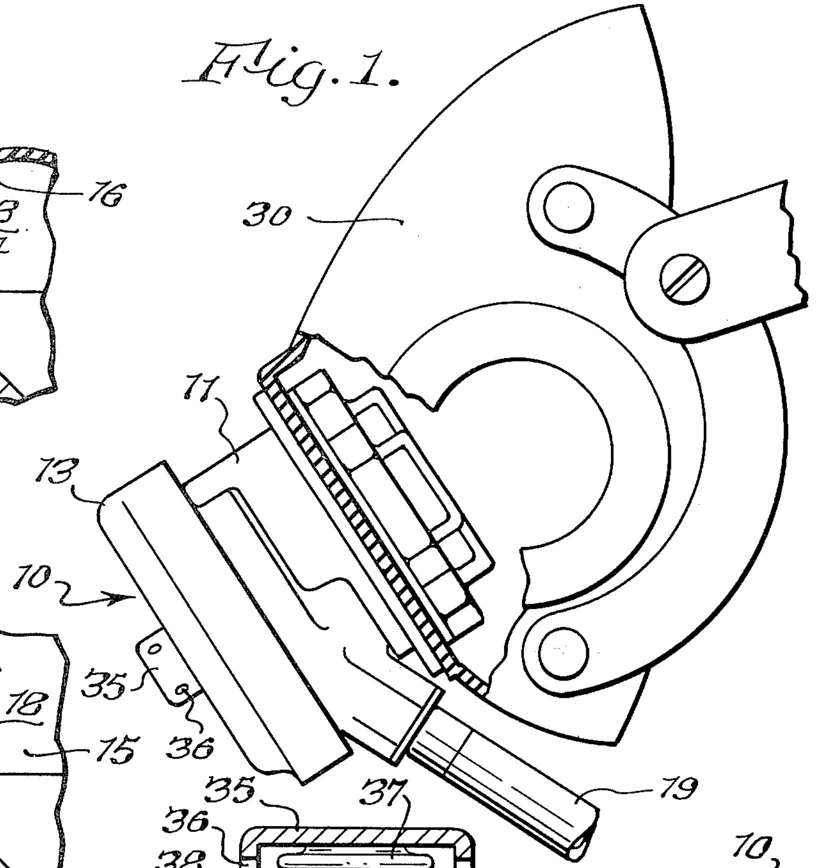
Fig. 4.
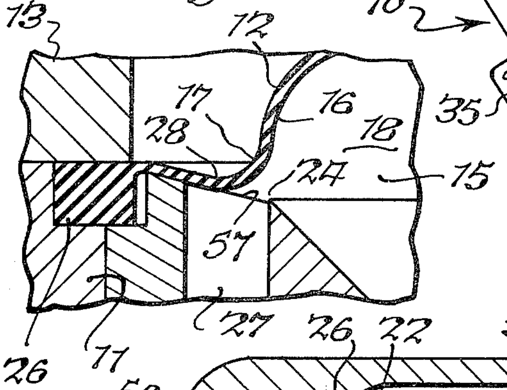
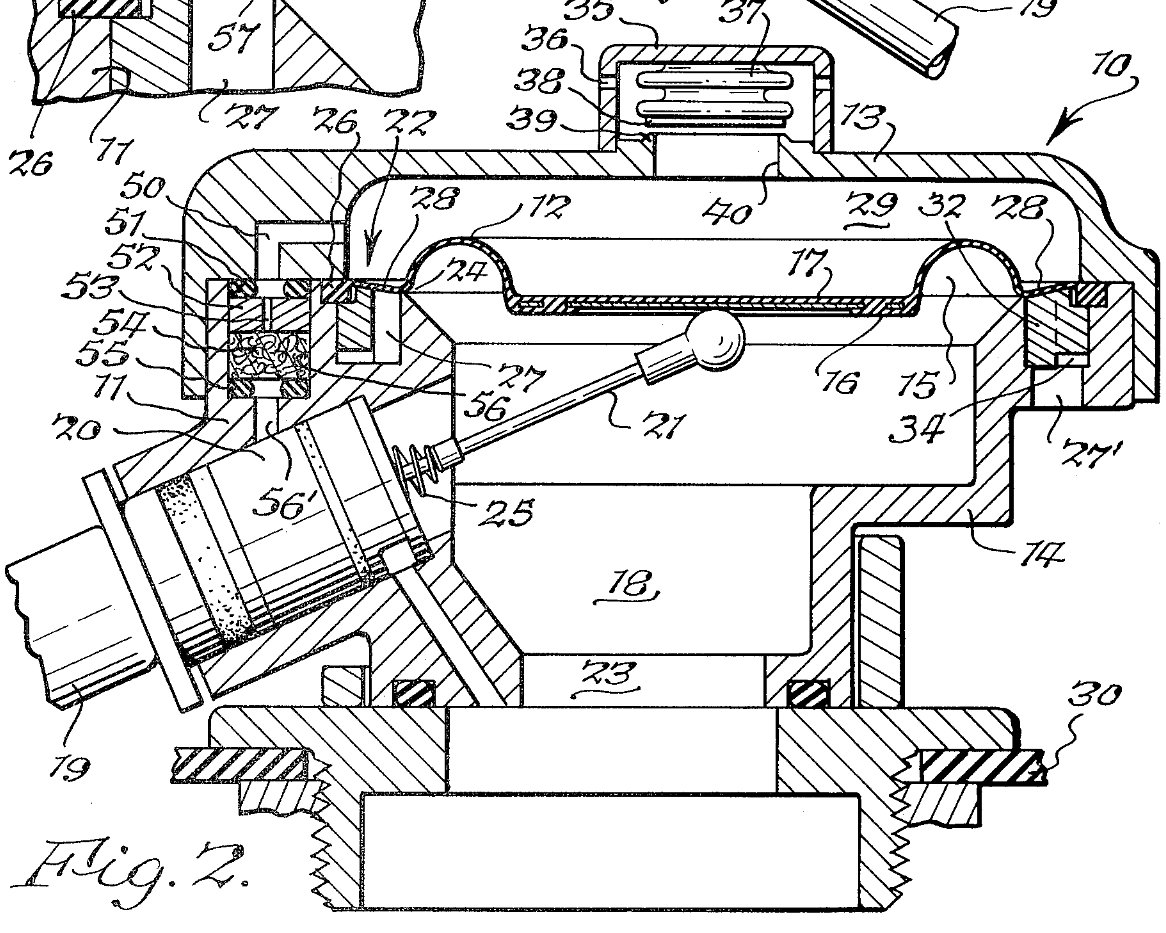
Fig. 2.

BREATHING VALVE ASSEMBLY WITH DIAPHRAGM CONTROL OF THE EXHAUST PORTS

BACKGROUND OF THE INVENTION (a) Field of the Invention

This invention relates to breathing apparatus of the type wherein breathing fluid is provided to a mask upon a demand evidenced by inhalation by the user of the mask.

(b) History of the Prior Art

In the prior art, demand type valves for use in conjunction with breathing masks have been provided which are responsive to inhalation by the mask user. In one type of such mask a flexible member in the form of a diaphragm moves in response to the reduced pressure created in the mask chamber upon inhalation and actuates a lever which in turn opens a breathing fluid supply valve. Such masks, as shown in the prior art customarily are provided with an independent exhaust valve which opens upon exhalation to permit the escape of gas exhaled by the mask user. The exhaled gas both moves the diaphragm to its normal position of rest and opens the independent exhaust valve.

BRIEF DESCRIPTION OF THE INVENTION

In accordance with the invention there is provided demand type breathing apparatus wherein the exhaust valve and the diaphragm are combined thus eliminating the need for an independent exhaust valve. The diaphragm controls both the inlet and the exhaust valves, opening the former in response to inhalation and the latter in response to exhalation.

The breathing apparatus of the invention comprises a hollow casing which is provided with an opening in the casing wall. A flexible diaphragm is positioned across the opening and in conjunction with the hollow casing forms a chamber. The diaphragm is movable in response to variations in differential pressure between the inside and outside of the chamber. A breathing fluid inlet valve communicates with the chamber and is opened in response to inward movement of the diaphragm resulting from a reduction of chamber pressure created upon inhalation by a user of the apparatus. An outlet valve is provided for exhausting fluid from the chamber when pressure within the chamber is increased above a predetermined value upon exhalation by the user.

The improvement of the invention comprises providing a sealing surface against which the diaphragm normally is sealingly engaged and from which at least a portion of the diaphragm is disengaged upon exhalation into the chamber. The diaphragm and the sealing surface act as the outlet valve with the diaphragm controlling both the inlet valve and the exhaust ports, thereby eliminating the need for a separate outlet or exhaust valve.

BRIEF DESCRIPTION OF THE DRAWING

FIG. 1 is a side elevational view of a breathing mask equipped with a breathing valve assembly of this invention.

FIG. 2 is a sectional view of the breathing valve assembly, on an enlarged scale.

FIG. 3 is a further enlarged, fragmentary sectional view of the exhaust valve in a partially open position.

FIG. 4 is similar to that of FIG. 3 showing the exhaust valve in a further open position.

DETAILED DESCRIPTION OF THE INVENTION

Referring now in detail to the embodiment depicted by way of illustration in the accompanying drawing, there is shown a breathing apparatus 10 which comprises a casing 11, a flexible diaphragm 12 and a cover 13. The casing may be made of any suitable rigid material which is essentially impervious to air and oxygen, such as steel, aluminum and rigid plastics, and which will not incorporate toxic substances into breathing fluids. The casing is defined by a casing wall 14 through which a first opening 15 is provided. Flexible diaphragm 12 having internal and external surfaces 16 and 17 respectively is positioned across opening 15. Flexible diaphragm 12 is manufactured from a flexible gas impervious material such as natural or silicone rubber or a flexible plastic.

Flexible diaphragm 12 in conjunction with casing 11 defines a chamber 18 into which a breathing fluid supply line 19 is connected through an inlet valve 20 of conventional design. Breathing fluid supply line 19 is connected to a source of breathing fluid, not shown, such as air or oxygen. Inlet valve 20 is opened in response to inward movements of diaphragm 12 by a tilt lever 21 which is moved by diaphragm 12 to open inlet valve 20 and which has a restoring spring 25 to close the valve upon outward movement of the diaphragm, all in a manner well known in the demand regulator art.

The apparatus is provided with an outlet valve 22 for venting or exhausting fluid from chamber 18 when fluid pressure within chamber 18 exceeds a predetermined level. A second opening 23 into chamber 18 is provided which is adapted for airtight communication with the breathing function of a user, usually through a close coupling to breathing mask 30 as shown. If desired, such communication can be through a tube or hose, not shown, one end of which is tightly connected with second opening 23 and the other end of which is connected to breathing mask 30.

In accordance with the invention, there is provided a sealing surface 24 about opening 15 against which a circumferential portion 28 of internal surface 16 of diaphragm 12 normally sealingly engages to close opening 15 and from which at least a portion of diaphragm 12 is disengaged when the pressure within chamber 18 increases above a predetermined level, thus permitting surface 16 of diaphragm 12 in conjunction with surface 24 to act as outlet valve 22.

Casing wall 14 is formed to provide an exhaust channel 31 around opening 15, communicating with chamber 18 when diaphragm 12 is disengaged from surface 24 and closed from communication with chamber 18 when diaphragm 12 sealingly engages surface 24. Channel 31 is vented to atmosphere through ports 27' at the bottom of the channel, and is subdivided into an annular series of exhaust ports 27 by an annular series of radial bars 32 joined at their outer periphery by a ring 33 having a recessed bottom wall providing an annular chamber 34 communicating with exhaust ports 27 and with vent ports 27'. Bars 32 are of substantial width or thickness, and with ring 33 provide an inwardly sloping, inverted frusto-conical support surface 57 for the circumferential portion 28 of diaphragm 12 when it is sealing engaged against surface 24 to close outlet 22, as shown in FIG. 2. The slope of surface 57 is such that its inner periphery is only slightly below the sealing surface 24 of casing wall 14, and its outer periphery is at diaphragm ring 26 or substantially so.

External surface 17 of diaphragm 12 is protected by cover 13 which is shaped to provide a chamber 29 on the side of diaphragm 12 opposite chamber 18 and which is provided with a vent 40 so that external surface 17 of flexible diaphragm 12 is usually constantly exposed to atmospheric pressure. Periphery 26 of diaphragm 12 is a thick ring securely held in the recessed upper ends of casing wall 14 and of ring 33 by cover 13 but diaphragm 12 is not held against sealing surface 24 by cover 13.

The diaphragm 17 is carefully designed so that in any orientation there is a preload built into a diaphragm sufficient to maintain contact with the sealing surface 24 with no differential pressure across the diaphragm. This means that a small positive pressure in chamber 18 must be induced to lift the diaphragm at sealing surface 24 and exhaust the exhaled gases through ports 27, 27'.

In its most common usage, the gas in chamber 29 simply moves in and out through port 40 as the differential pressure across diaphragm 12 is altered by an induced negative or positive pressure in chamber 18. It is within the scope of the invention, however, that a positive pressure (above ambient) may be imposed on the diaphragm by some secondary device, as described below. However, the design is such that the differential pressure across diaphragm 12 needed to either open the demand valve 20 or in turn to lift diaphragm 17 from sealing edge 24 to exhaust gases, will remain almost constant. This is accomplished by the radial supports 32, 33 which are incorporated in exhaust channel 31, so that the effective area of the diaphragm subject to the differential pressure remains in a substantially constant ratio of 1:1.

When the regulator is of the pressure-demand type, to avoid any possibility of inboard leakage for example, an orificed flow of gas from the upstream side of inlet valve 20 to chamber 29 can be provided. As shown in FIG. 2, cover 13 can have a passage 50 communicating with chamber 29 and with a passage 56' in casing 11 communicating with the inlet supply. Casing 11 also has a bore 56 communicating with passage 56' and containing an orifice button 52 having a restricted orifice 53 communicating with passage 56' through a filter 54. The opposite ends of bore 56 are sealed around passages 50 and 56' by O rings 51 and 55. With this arrangement a constant supply of inlet gas is bled to chamber 29, biasing diaphragm 12 to maintain a positive pressure in chamber 18 in a manner known in the art. An aneroid 37 in a cap 35 on cover 13 carries a valve 38 adapted to engage a seat 39 around port 40, the cap having vent openings 36 to atmosphere. Port 40 and valve 38 are of a diameter approximately equal to the diameter of aneroid 37, whereby aneroid 37 and the pressure in chamber 29 act against the same valve area.

Support surface 57 is useful but not essential when operating in the straight demand mode and diaphragm 12 is subject only to ambient atmospheric pressure in chamber 29. When operating in the pressure demand mode, however, supporting surface 57 is necessary to maintain the desired uniform opening action of outlet 22 in response to increased pressure on surface 16 of diaphragm 12.

In operation, when the user of apparatus 10 inhales, the pressure within chamber 18 is reduced which causes the center of diaphragm 12 to move inwardly, activating lever 21 which in turn opens inlet valve 20 thus permitting breathing fluid to enter chamber 18. This reinforces the self-sealing action of diaphragm 12 against surface 24, keeping outlet valve 22 closed. When the user of breathing apparatus 10 exhales, the pressure in chamber 18 is increased and diaphragm 12 moves outwardly permitting inlet valve 20 to close. However, outlet valve 22 remains closed and circumferential portion 28 of diaphragm 12 does not lift away from sealing surface 24 until the pressure within chamber 18 exceeds that within chamber 29 by an amount sufficient to overcome the built-in preload or self-sealing bias of diaphragm 12 whereupon diaphragm portion 28 is lifted from supporting surface 57 permitting exhaled gas to pass between internal surface 16 of diaphragm 12 and sealing surface 24 through exhaust ports 27 and vents 27' to the outside of apparatus 10. The amount of diaphragm portion 28 which is lifted from surface 57 increases with the pressure force of exhalation, thereby increasing the area of exhaust opening through ports 27 as shown by comparing FIGS. 3 and 4.

Thus, the inlet valve actuating diaphragm 12 also controls the exhaust outlet. The inlet 20 is opened by the diaphragm upon inhalation to admit breathing fluid to the chamber, the outlet 22 remaining closed by the diaphragm. The outlet is opened by the diaphragm upon exhalation, after permitting the inlet to close, to vent the products of exhalation from the chamber. The diaphragm 12, in conjunction with the peripheral sealing surface 24 provides the outlet valving action. The truncated, inverted conical shape of surface 57 supports diaphragm portion 28, at rest and during inward movement of the diaphragm, and also during lifting of portion 28 away from surface 24 upon outward movement of the diaphragm.

I claim:

1. In a breathing apparatus having a hollow casing with an opening in one wall thereof, a flexible diaphragm secured at its periphery relative to said casing and having internal and external surfaces positioned across said opening, said diaphragm forming a chamber in conjunction with said casing and being movable in response to variations in differential pressure across said diaphragm, a breathing fluid inlet to said chamber, means for opening said inlet responsive to movement of said diaphragm inwardly of said chamber upon a reduction of pressure within said chamber, a fluid outlet from said chamber and means for opening said outlet when pressure within said chamber exceeds a predetermined relative pressure, the improvement wherein said means for opening comprises arranging said diaphragm and said outlet so that said diaphragm itself normally closes said outlet and maintains said outlet closed until the chamber pressure exceeds a predetermined value whereupon movement of said diaphragm outwardly of said chamber opens said outlet to vent fluid from said chamber.

2. Breathing apparatus is defined in claim 1, said apparatus being of the straight demand type.

3. Breathing apparatus as defined in claim 1, said apparatus being of the pressure-demand type.

4. Breathing apparatus as defined in claim 1, said means for opening said inlet including a tilt valve having a stem engaged by said diaphragm upon inward movement thereof to open said valve and spring means biasing said valve to inlet closing position.

5. Breathing apparatus as defined in claim 1, together with a sealing surface about said opening against which a portion of the internal surface of said diaphragm normally sealingly engages to close said outlet and from which at least a portion of said diaphragm is disengaged when the pressure within said chamber exceeds a predetermined value, said diaphragm and said surface thereby acting as an outlet valve.

6. Breathing apparatus as defined in claim 5, said diaphragm having a built-in pre-load sufficient to maintain said outlet valve normally closed in all positions of orientation of said apparatus.

7. In a breathing apparatus having a hollow casing with an opening in one wall thereof, a flexible diaphragm secured at its periphery relative to said casing and having internal and external surfaces positioned across said opening, said diaphragm forming a chamber in conjunction with said casing and being movable in response to variations in differential pressure across said diaphragm, a breathing fluid inlet to said chamber, means for opening said inlet responsive to movement of said diaphragm inwardly of said chamber upon a reduction of pressure within said chamber, a fluid outlet from said chamber and means for opening said outlet when pressure within said chamber exceeds a predetermined relative pressure, the improvement wherein said means for opening comprises arranging said diaphragm and said outlet so that said diaphragm itself normally closes said outlet and maintains said outlet closed until the chamber pressure exceeds a predetermined value whereupon said diaphragm opens said outlet to vent fluid from said chamber, wherein said external surface of said diaphragm is protected by a cover defining with said diaphragm a second chamber, said second chamber being vented to the exterior of said apparatus.

8. Breathing apparatus as defined in claim 7, said diaphragm having a built-in pre-load sufficient to maintain said outlet valve normally closed in all positions of orientation of said apparatus.

9. Pressure-demand breathing apparatus as defined in claim 7, together with means for maintaining a positive pressure within said second chamber relative to ambient atmosphere.

10. Pressure-demand breathing apparatus as defined in claim 9, wherein said means for maintaining a positive pressure include a bleed passage from said inlet to said second chamber, and aneroid means controlling the vent from said second chamber.

11. Pressure-demand breathing apparatus as defined in claim 9, said outlet comprising a series of alternating ports and support means around said opening, and a sealing surface arround said opening inwardly of said ports and support means, said internal surface of said diaphragm normally sealingly engaging said sealing surface to close said outlet, said support means providing support for said diaphragm outwardly of said sealing surface.

12. In a breathing apparatus having a hollow casing with an opening in one wall thereof, a flexible diaphragm secured at its periphery relative to said casing and having internal and external surfaces positioned across said opening, said diaphragm forming a chamber in conjunction with said casing and being movable in response to variations in differential pressure across said diaphragm, a breathing fluid inlet to said chamber, means for opening said inlet responsive to movement of said diaphragm inwardly of said chamber upon a reduction of pressure within said chamber, a fluid outlet from said chamber and means for opening said outlet when pressure within said chamber exceeds a predetermined relative pressure, the improvement wherein said means for opening comprises arranging said diaphragm and said outlet so that said diaphragm normally closes said outlet and maintains said outlet closed until the chamber pressure exceeds a predetermined value whereupon said diaphragm opens said outlet to vent fluid from said chamber, together with a sealing surface about said opening against which a portion of the internal surface of said diaphragm normally sealingly engages to close said outlet and from which at least a portion of said diaphragm is disengaged when the pressure within said chamber exceeds a predetermined value, said diaphragm and said surface thereby acting as an outlet valve, said outlet comprising a series of alternating ports and support means around said opening, said sealing surface being interposed between said series of outlet ports and said opening, and said opening, and said support means providing support for said diaphragm outwardly of said sealing surface.

13. Breathing apparatus as defined in claim 12, said apparatus being of the pressure-demand type having means for maintaining a positive pressure relative to ambient atmosphere on said external surface of said diaphragm.

* * * * *